United States Patent [19]

Guglielmetti et al.

[11] Patent Number: 5,233,038

[45] Date of Patent: Aug. 3, 1993

[54] PHOTOCHRONIC COMPOUNDS OF THE INDOLINO-SPIRO-BENZOXAZINE TYPE

[75] Inventors: Robert Guglielmetti, Marseille; Pascale Tardieu, Paris, both of France

[73] Assignee: Essilor International (Compagnie Generale d'Optique), Creteil, France

[21] Appl. No.: 802,666

[22] Filed: Dec. 5, 1991

[30] Foreign Application Priority Data

Dec. 6, 1990 [FR] France .................. 90 15324

[51] Int. Cl.$^5$ ................................ G02B 5/23
[52] U.S. Cl. ......................... 544/99; 544/101
[58] Field of Search ................ 544/101, 102, 99

[56] References Cited

U.S. PATENT DOCUMENTS

| | | | |
|---|---|---|---|
| 3,929,783 | 12/1975 | Krapdio et al. | 260/243 R |
| 4,699,473 | 10/1987 | Chu | 544/71 |
| 4,720,547 | 1/1988 | Kwak et al. | 544/71 |

FOREIGN PATENT DOCUMENTS

| | | |
|---|---|---|
| 0245020 | 11/1987 | European Pat. Off. . |
| 0339661 | 11/1989 | European Pat. Off. . |
| 0358774 | 3/1990 | European Pat. Off. . |
| WO87/00524 | 1/1987 | PCT Int'l Appl. . |

*Primary Examiner*—Nicholas S. Rizzo
*Attorney, Agent, or Firm*—Millen, White, Zelano & Branigan

[57] ABSTRACT

The invention relates to novel photochromic compounds of the family of indolino-spiro-oxazines, these compounds being distinguished by the fact that they correspond to the formula of an indolino-spiro-benzo-cyclodiazene.

12 Claims, No Drawings

PHOTOCHRONIC COMPOUNDS OF THE INDOLINO-SPIRO-BENZOXAZINE TYPE

The object of the present invention is to provide novel compounds which are of the indolino-spiro-oxazine type and which have useful photochromic properties. The invention is also concerned with a method of preparation of these compounds as well as their industrial applications as photochromic additives, particularly in the manufacture of transparent photochromic articles.

A number of different photochromic compounds belonging to the chemical family of spiro-oxazines are already known, including those having the formula of an indolino-spiro-benzoxazine as given below:

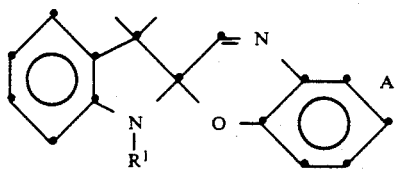
(I)

where $R^1$ is an alkyl radical and the indoline and oxazine nuclei are capable of carrying various substituents, in particular lower alkyl radicals (containing 1 to 5 carbon atoms) which do not affect their essential properties.

However, there is still a great need to achieve improvements in the techniques of manufacture of photochromic compounds and to discover novel compounds having specific properties which are different from those of known compounds.

Considering in particular the field of manufacture of organic glasses or lenses which are capable of becoming tinted in sunlight, it is an advantage to provide a very wide range of photochromic additives which differ from each other, for example, in their properties of compatibility with any particular organic resin, in the absorption spectrum of the tinted form, and so on, while at the same time meeting other requirements such as speed of tinting and de-tinting, chemical stability, resistance to conditions of use involving a large number of sequences of tinting and de-tinting in the course of time and insensitivity to temperature variations.

The compounds in accordance with the invention are indolino-spiro-benzocyclodiazenes or in other words compounds corresponding to Formula I in which the group A contains a diazene bond ring —N=N—, preferably in a triaza five-membered ring orthocondensed on an aromatic ring. In this respect they are distinguished from other compounds proposed in the prior art, in particular from those in which the group A orthocondensed on the benzene nucleus of the oxazine portion of the molecule is an aromatic nitrogenized heterocycle among those disclosed in U.S. Pat. No. 4,720,547, or from those in which said group A is of the benzofuran type as in European patent No. 0,358,774.

The preferred photochromic compounds of the invention include in group A a triazole ring. They advantageously have the general formula:

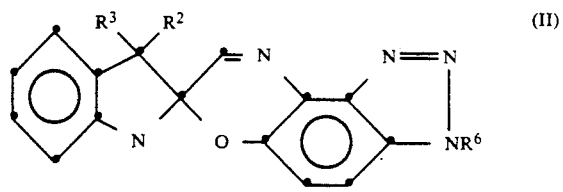
(II)

where $R^6$ is a hydrogen atom, a phenyl, an alkyl radical, especially an alkyl radical containing 1 to 5 carbon atoms, $R^1$ an alkyl radical, especially an alkyl radical containing 1 to 8 carbon atoms such as in particular the methyl and isopropyl groups, $R^2$ and $R^3$ may in each case, and independently of each other, be any one of the conventional substituents in the indolino-spiro-benzoxazine compounds of the prior art, in particular an alkyl or alkoxy radical containing 1 to 5 carbon atoms.

The phenyl groups which are included respectively in the indoline portion and in the oxazine portion of the molecule can also each contain one or a number of substituents of any type which does not have any disturbing effect on the essential properties of the compound.

The invention therefore extends in particular to the homologs of the compounds of Formula (II) in which:

$R^1$ represents
1) an alkyl group containing 1 to 16 carbon atoms such as a group comprising methyl, ethyl, n-propyl, isopropyl, n-butyl;
2) a group comprising allyl, phenyl, arylalkyl such as a group comprising benzyl, phenyl monosubstituted and disubstituted by substituents of the alkyl or alkoxy type containing 1 to 6 carbon atoms;
3) an alicyclic group such as a cyclohexyl group which may be substituted;
4) an aliphatic hydrocarbon group including in its chain one or a number of heteroatoms such as O, N or S, in particular an acid, ester or alcohol function;

$R^2$ and $R^3$ may each represent independently of the other as $C_{1-8}$ group comprising alkyl, phenyl, phenyl monosubstituted and disubstituted by $C_{1-4}$ alkyl and/or $C_{1-5}$ alkoxy groups or can be combined so as to form a ring chain of 6 to 8 carbon atoms (including spirane-3 carbon of the indoline heterocycle).

If $R^4$ designates the four possible substituents on the benzene nucleus of the indoline portion of the molecule and $R^5$ designates the two possible substituents of the benzene nucleus of the oxazine portion, then in a general manner $R^4$ and $R^5$ may each represent independently of the other:
1) a hydrogen atom, an amine function NR'—R", where R' and R" each represent independently a hydrogen atom, a group comprising alkyl, cycloalkyl, phenyl or a substituted derivative of this latter; R' and R" can combine so as to form a cycloalkyl which can be substituted and contain one or a number of heteroatoms;
2) an R, OR, SR, COR or COOR group in which R represents a hydrogen atom, an alkyl group containing 1 to 6 carbon atoms or an aryl or heteroaryl group;
3) a halogen atom, a monohaloalkyl $C_{1-4}$ group, a polyhaloalkyl $C_{1-4}$ group such as CF3, the halogen being especially Cl, Br;

4) $-NO_2$, CN, SCN;

in which each of the substituents $R^4$ can be present on any one of the suitable carbon atoms of the indoline portion of the photochromic compound at positions 4, 5, 6 and 7 when the other is a hydrogen atom whereas it is preferable that two substituents other than a hydrogen atom should be present at positions 4 and 5, 5 and 6, 4 and 6 or 6 and 7.

Preferably:

$R^1$ is a $C_{1-4}$ group comprising alkyl, phenyl or benzyl;

$R^2$ and $R^3$ are selected from the alkyl $C_{1-5}$ groups such as methyl and ethyl or a phenyl group or are combined so as to form a cyclohexyl group;

each group $R^4$ is selected from the group constituted by hydrogen, $C_{1-2}$ alkyl, chlorine, fluorine, bromine, iodine, $C_{1-2}$ trihaloalkyl and $C_{1-5}$ alkoxy;

and $R^5$ is a hydrogen atom or an alkoxy $C_{1-4}$ group or a tertiary amine or a halogen.

The compounds in accordance with the invention which are particularly advantageous include those in which:

$R^1$ is an alkyl $C_{1-4}$ group such as methyl, ethyl, isopropyl or n-butyl;

$R^2$ and $R^3$ each represent independently of the other a methyl, ethyl or phenyl group;

$R^4$ is a hydrogen atom, a methyl, methoxy or chloro group;

and $R^5$ is a hydrogen atom.

Among other particularly suitable applications of the compounds in accordance with the invention, it is of special interest to mention the use of photochromic additives in the manufacture of disks for recording optical information such as those commonly designated as laser disks.

In this case, it is desirable to ensure that the diazene ring of the molecule includes a proton or in particular that $R^6$ is a hydrogen atom in Formula II.

Moreover, a fact observed in practice is that it is often an advantage to make use of compounds in which the indoline portion of the molecule contains a nitro substituent, preferably at the 5 position of the indoline group. In particular, the photochromic colorability is appreciably increased when, in Formula II, the $R^4$ substituent is $NO_2$.

The compounds in accordance with the invention can be obtained by a method of preparation which utilizes methods of synthesis already known per se and which involves a step of condensation of an indoline III base on a nitroso-hydroxy-heteroaromatic IV compound in accordance with the diagram:

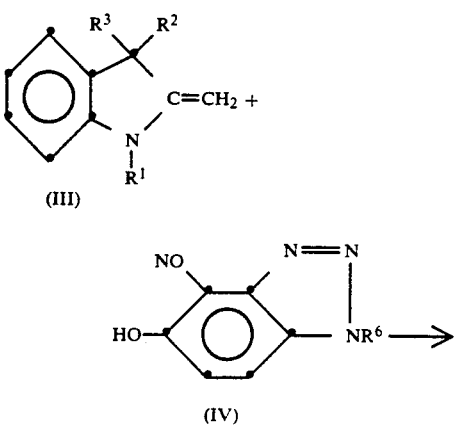

The intermediate compound (IV) can be obtained beforehand by hydrolysis of a suitable derivative which is thus converted to a corresponding hydroxy derivative followed by nitrosation of this latter. The suitable hydroxy derivative can in turn be obtained from para-aminophenol by means of successive steps of acetylation, nitration, catalytic reduction which converts $NO_2$ to $NH_2$, and condensation so as to form the triazole ring. The acetoxy-5-acetyl-1-benzotriazole obtained at this stage can be deacetylated by hydrolysis in a strong acid medium in order to produce the hydroxy-5-benzotriazole which is sought for nitrosation.

The compounds employed in accordance with the present invention for the preparation of photochromic compositions can be dissolved in a suitable solvent such as toluene or ethanol in order to obtain a photochromic solution. The same photochromic compounds can also be dissolved within a polymer, a copolymer or a mixture of polymers in solution in a suitable organic solvent.

They accordingly serve to constitute compositions in accordance with the present invention which can be applied or introduced in or on a transparent organic polymer material in order to obtain a transparent photochromic article. This material is preferably of optical quality and is more particularly suitable for the manufacture of ophthalmic lenses.

In addition, they can make up photochromic compositions which also form the subject of the present invention and can be employed directly in the formation of photochromic plastic films, of plates and of lenses such as lenses for sunglasses, viewfinders, camera lenses and filters.

Examples of suitable compositions in accordance with the invention for the manufacture of transparent photochromic materials and articles include one or a number of the photochromic compounds of the present invention in combination with one or a number of the following polymers: polymer of a polyolallylcarbonate monomer, polyacrylate, polyalkylacrylates such as polymethyl methacrylate (PMMA), cellulose acetate, cellulose triacetate, cellulose acetate propionate and butyrate, polyvinyl acetate, polyvinyl alcohol, polyurethanes, polycarbonates, polyethyleneterephthalate, polystyrene, copolymers of styrene and of methyl methacrylate, acrylonitrile, polyvinylbutyral.

The quantity of photochromic compound (or of composition containing this compound) applied or introduced on or in the polymer material is not of critical importance and usually depends on the desired color intensity under irradiation and on the method employed for incorporating or applying the photochromic compound. This method can be selected from the numerous methods which are applicable to the photochromic compounds of the prior art, including in particular dissolution or dispersion of the compound in the basic composition of the material, or formation of a photochromic layer at the surface or within a transparent supporting material.

Generally speaking, as the quantity of photochromic compound added is larger, so the coloring or tinting under irradiation will be greater. This quantity may be described as a photochromic quantity. In the usual manner, the quantity of photochromic compound incorporated in the optical material is from 0.01 to 20% by weight and preferably from 0.05 to 10% by weight with respect to the total weight of optical material.

There are thus obtained photochromic effects which result in the appearance of a tint under the action of exposure to radiations in the ultraviolet region with a return to the original color or transparency when exposure to ultraviolet radiations is interrupted. This change of coloring can be renewed a very large number of times as is required in the case of glasses which provide protection from sunlight. Moreover, the coloring persists throughout the time of exposure to solar radiation with a higher degree of reliability than in the case of photochromic compounds of the prior art.

The invention will now be more fully illustrated by means of particular examples of application which are not given in any limiting sense.

EXAMPLE I

Synthesis of
Trimethyl-indolino-spirobenzotriazole-oxazine

1) Synthesis of hydroxy-5-nitroso-4-benzotriazole

Acetoxy-4-acetylamino-1-benzene

To an agitated solution of 0.05 mole of p-aminophenol in 50 ml of 3M NaOH, there are rapidly added 15 ml of acetic anhydride and 5 to 10 g of crushed ice. Vigorous agitation is maintained for a few minutes. A beige precipitate appears which is collected and purified if necessary by chromatography (eluant: $CHCl_3/CH_3OH$).

| Yield | 80% |
|---|---|
| Melting point | 152° C. |
| Molecular weight | 193 g |
| Empirical formula | $C_{10}H_{11}NO_3$ |

Nuclear magnetic resonance (NMR) analysis and infrared spectroscopy reveal the developed formula of acetoxy-4-acetyl-amino-1-benzene.

Acetoxy-4-acetylamino-1-nitro-2-benzene 1.93 g of acetoxy-4-acetylamino-1-benzene obtained (0.01 mole) are added in small portions to ml of fuming nitric acid, agitated at low temperature (ice bath+salt, T=0°-5° C).

Over a period of 20-25 minutes, the reaction medium is then maintained at a temperature within the range of 12° to 15° C., then poured onto crushed ice (hydrolysis).

The bright yellow solid which precipitates is collected and recrystallized in ethanol, then analyzed by nuclear magnetic resonance and by infrared spectroscopy in solution in chloroform.

| Yield prior to recrystallization | 97% |
|---|---|
| Melting point | 142° C. |
| Molecular weight | 238 g |
| Yield after recrystallization | 68% |
| Empirical formula | $C_{10}H_{10}N_2O_5$ |

| Melting point | 144° C. |
|---|---|

Acetoxy-4-acetylamino-1-amino-2-benzene

A mixture containing 2.38 g of acetoxy-4-acetylamino-1-nitro-2-benzene obtained (0.01 mole), 6 ml of cyclohexene, palladium on 10% charcoal (in catalytic quantity) in 20 ml of ethanol, is heated and refluxed overnight in a hydrogen atmosphere.

The following day, the mixture is filtered in the hot state on celite in order to eliminate the catalyst. As the filtrate cools, there is observed the appearance of a white precipitate which is collected and purified by recrystallization in absolute ethyl alcohol. Nuclear magnetic resonance analysis and infrared analysis show that this precipitate is acetoxy-4-acetylamino-1-amino-2-benzene.

| Yield | 64% |
|---|---|
| Melting point | 174° C. |
| Molecular weight | 208 g |
| Empirical formula | $C_{10}H_{12}N_2O_3$ |

Acetoxy-5-acetyl-1-benzotriazole

A solution of 0.7 g of sodium nitrite $NaNO_2$ (0.01 mole) in 2.7 ml of distilled water is added very slowly to a solution of 2.08 g of acetoxy-4-acetylamino-1-amino-2-benzene (0.01 mole), 1.9 ml of concentrated hydrochloric acid, and 10 ml of distilled water, maintained at 0° C.

An orange precipitate is formed as the addition takes place. The precipitate is collected, 25 filtered and washed with water.

| Yield | 94% |
|---|---|
| Melting point | 125° C. |
| Molecular weight | 219 g |
| Empirical formula | $C_{10}H_9N_3O_3$ |

Hydroxy-5-benzotriazole hydrochlorate

A mixture of 2.19 g (0.01 mole) of acetoxy-5-acetyl-benzotriazole in 7 ml of concentrated hydrochloric acid is heated and refluxed until complete solubilization.

The solution is then cooled to low temperature (0° C.). A precipitate is formed, then collected and washed with distilled water.

| Yield | 65% |
|---|---|
| Melting point | 220° C. |
| (m.p. in literature | 225° C.) |
| Molecular weight | 171.5 g |
| Empirical formula | $C_6H_5N_3O$ |

Hydroxy-5-nitroso-4-benzotriazole

A mixture of 0.69 g of $NaNO_2$ (0.001 mole) in 5 ml of distilled water is added in 15 minutes to a solution of 1.72 g (0.001 mole) of hydroxy-5-benzotriazole hydrochlorate in 5 ml of distilled water, maintained at 0° C. by a bath of ice on salt.

When the addition has been completed, agitation is continued at low temperature over a period of one hour.

The orange-yellow solid which has formed is then filtered and dried.

| Yield | 95% |
|---|---|
| Molecular weight | 164 g |
| Empirical formula | $C_6H_4N_4O_2$ |

2) Synthesis of trimethyl-indolino-spirobenzotriazole-oxazine 0.003 mole of the indoline base having the formula trimethyl-1,3,3-methylene-2-indoline is heated and refluxed in 20 ml of a solvent consisting in this case of absolute ethyl alcohol. 0.003 mole of hydroxy-5-nitroso-4-benzotriazole in suspension in 60 ml of solvent is added slowly over a period of 1 hour and 30 minutes. Refluxing is continued over a period of 2 hours and 30 minutes.

As the reaction proceeds, the water is removed with the solvent by formation of an azeotrope (involving the use of Dean-Stark equipment). Unreacted nitrosed starting product is recovered on completion of the reaction in a proportion of 22% by weight.

The product obtained is purified by chromatography on silica in an eluant consisting of a mixture of ether-/ethyl acetate. It corresponds to the developed formula II where $R^1=R^2=R^3$, all three being —$CH_3$.

| Molecular weight | 319 g |
|---|---|
| Empirical formula | $C_{18}H_{17}N_5O$ |

EXAMPLE II

Synthesis of Isopropyl-dimethyl-indolino-spirobenzotriazole-oxazine

The same procedure as in Example II is applied in order to cause condensation of the product of Example I with the indoline base isopropyl-1-methylene-2-dimethyl-3,3-indoline.

There is thus obtained the isopropyldimethyl homolog having the formula II where $R^1$ is the isopropyl radical and both $R^2$ and $R^3$ are the methyl radical.

| Yield | 6% |
|---|---|
| Recovered reagent | 20% |
| Melting point | 196.5–197° C. |
| Molecular weight | 347 g |
| Empirical formula | $C_{20}H_{21}N_5O$ |

EXAMPLE III 5 The photochromic properties of the compounds in Examples I and II (case in which $R^6=H$) are examined.

The technique employed proceeds by flash photolysis and makes it possible to record the absorption spectrum of the open form (photomerocyanine) in the zone 400–650 nm, as well as its variation with time.

There are thus determined:
Ao: maximum optical density after photolysis,
$K_A$: constant kinetics of de-tinting (expressed in $s^{-1}$) as well as the wavelengths λe at the shoulder and λmax at the absorption peak, expressed in nanometers.

1) Measurements carried out in toluene

The measurements are performed at a temperature of 25° C. The energy of photolysis at 6 KV is approximately 60 joules. Ao is given for a concentration of $2.5 \times 10^5$ mole/l. The following results are obtained:
Compound of Example I:
Ao=0.14,
$K_A=0.17$ $s^{-1}$.
Compound of Example II:
Ao=0.37,
$K_A=0.18$ $s^{-1}$.

The data of the series V and VI given below are supplied by way of comparison with the state of the technique:

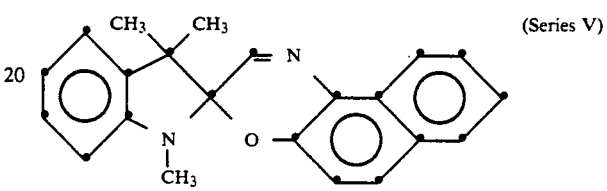
(Series V)

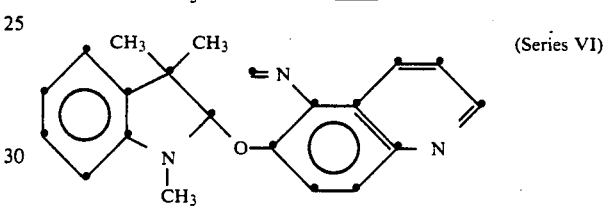
(Series VI)

By choosing toluene as solvent, the following characteristic wavelengths extracted from the absorption spectrum are obtained:
In the case of Series (V), the wavelength corresponding to the shoulder of the curve (λe) is 564 nm, the maximum wavelength (λmax) corresponding to the value of the wavelength at the absorption peak is 594 nm;
In the case of Series (VI): λe=561 nm, λmax=590 nm;
In the case of the compound of the invention (with $R^6=H$), the formula is as follows:

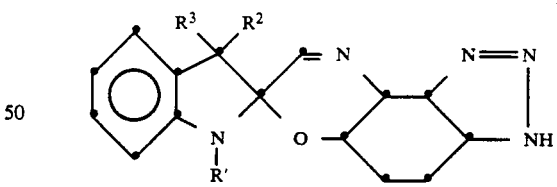

when $R^1=CH_3$: λe=595 nm, λmax=563 nm
when $R^1=i-C_3H_7$: λ3=598 nm, λmax=563 nm.

In the case of the compounds of the prior art which serve as a reference, it is found that maximum absorption is obtained at the longest wavelength whereas the situation is reversed in the case of the compound in accordance with the invention.

2) Influence of the solvent

The measurements are made successively in cyclohexane (a), toluene (b), dimethyl-sulfoxide (c).

By way of reference, consideration is given to a known compound which is a spiro(indolinephenanthrenoxazine) having the formula:

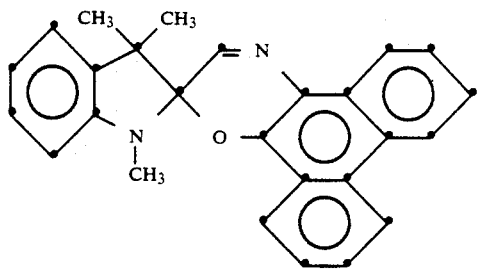

there is obtained:

in solvent (a): $\lambda e = 528$ nm, $\lambda max = 558$ nm
in solvent (b): $\lambda e = 538$ nm, $\lambda max = 574$ nm
in solvent (c): $\lambda e = 552$ nm, $\lambda max = 591$ nm In the case of this compound, the characteristic curve of the absorption spectrum of the open form is the same irrespective of the solvent employed.

In contrast, the compound in accordance with the invention has an absorption spectrum of its open form which exhibits a marked sensitivity to its environment and especially to the solvent in this instance. The absorption peak Ao corresponds in the apolar media to the short wavelengths and conversely in the polar media (in particular in dipolar aprotic solvents).

When $R_1 = i\text{-}C_3H_7$, $R_6 = H$, $R_2 = R_3$, $R_4 = R_5 = H$ (Example II), there is obtained:

in solvent (a): $\lambda e = 595$ nm, $\lambda max = 563$ nm
in solvent (b): $\lambda e = 598$ nm, $\lambda max = 565$ nm
in solvent (c): $\lambda e = 569$ nm, $\lambda max = 604$ nm It is found that, in dipolar aprotic solvents, the spectrum obtained after the photolysis flash exhibits a long-wavelength absorption peak, then changes in an unusual manner. There is observed an interconversion phenomenon having a time-duration of 250 ms in dimethylsulfoxide at 25° C. which progressively gives rise to inversion of the absorption bands.

The new spectrum thus obtained (comparable with that recorded in an apolar medium) then undergoes a decrease in time corresponding to conventional thermal decolorizing.

The phenomenon just mentioned (rapid change of $\lambda max$ as a result of light excitation) can find applications in the field of storage of information (computer memories, optical disks).

As will be readily apparent, the invention is not limited in any sense to the particular features which have been specified in the foregoing examples or to the details of the particular modes of execution which have been chosen in order to illustrate the invention. All kinds of alternative arrangements can be made in the operating conditions as well as in the nature and proportions of the constituents and reagents without thereby departing from the scope of the invention.

What is claimed is:

1. A photochromic compound of the formula (II):

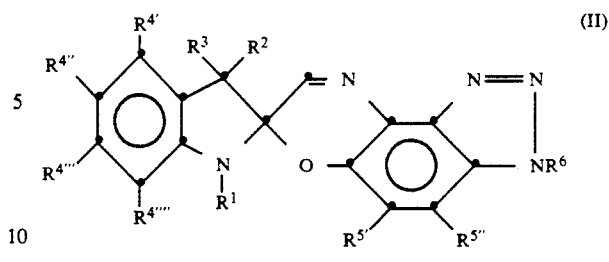

wherein,
$R^1$ is an alkyl or allkyl radical of 1 to 16 carbon atoms which may optionally be interrupted in its chain by one or more O, S or N heteroatoms or an acid, ester or alcohol function, a phenyl or phenylalkyl radical wherein the phenyl rings are optionally substituted by alkyl or alkoxy radicals of 1 to 6 carbon atoms or an alicyclic group of 1 to 16 carbon atoms, $R^2$ and $R^3$ are, independently of the other, an alkyl radical of 1 to 8 carbon atoms or phenyl optionally substituted by $C_1\text{-}C_4$ alkyl groups, $C_1\text{-}C_5$ alkoxy groups or mixtures thereof, or $R^2$ and $R^3$ combine to form a ring of 6 to 8 carbon atoms including the spirane-3 carbon of the indoline ring, the $R^4$ groups are independently selected from a hydrogen atom, a halogen atom, a $C_1\text{-}C_4$ monohaloalkyl radical, a $C_1\text{-}C_4$ polyhaloalkyl radical, $-NO_2$, $-CN$, $-SCN$, an R, OR, SR, COR, or COOR radical wherein R is a hydrogen atom, an alkyl group containing 1 to 6 carbon atoms or a carbocyclic aryl group, or an amine radical NR'R" wherein R' and R" are independently selected from a hydrogen atom, alkyl, cycloalkyl, or phenyl group, or R' and R" combine together with the nitrogen atom to form a cycloalkyl ring which may further contain one or more endocyclic O, S or N heteroatoms, the $R^5$ groups have the same meaning as set forth for the $R^4$ groups, and $R^6$ is a hydrogen atom, phenyl or an alkyl radical containing 1 to 5 carbon atoms.

2. The photochromic compound of claim 1, wherein the radical $R^6$ is a hydrogen atom.

3. The photochromic compound of claim 1, wherein:
$R^1$ is a $C_1\text{-}C_4$ alkyl group, phenyl or benzyl;
$R^2$ and $R^3$ are independently selected from $C_1\text{-}C_5$ alkyl groups or a phenyl group or are combined so as to form a cyclohexyl group;
each group $R^4$ is independently selected from hydrogen, $C_1\text{-}C_2$ alkyl, chlorine, fluorine, bromine, iodine, $C_1\text{-}C_2$ trihaloalkyl and $C_1\text{-}C_5$ alkoxy;
each $R^5$ group is independently selected from a hydrogen atom, a $C_1\text{-}C_4$ alkoxy group, a tertiary amine or a halogen.

4. The photochromic compound of claim 1, wherein:
$R^1$ is a methyl group or isopropyl group;
$R^2$ and $R^3$ each represent a methyl group.

5. The photochromic compound of claim 1, wherein at least one of the $R^4$ groups is $-NO_2$.

6. The photochromic compound of claim 5, wherein $R^{4''}$ radical is $-NO_2$.

7. The photochromic compound of claim 1 wherein either $R^{4'}$ and $R^{4''}$, $R^{4''}$ and $R^{4'''}$, $R^{4'}$ and $R^{4'''}$, or $R^{4'''}$ and $R^{4''''}$ are other than hydrogen.

8. The photochromic compound of claim 1 wherein at least one of the $R^4$ groups is $CF_3$.

9. The photochromic compound of claim 1 wherein at least one of the $R^4$ groups is Cl or Br.

10. The photochromic compound of claim 1 wherein $R^1$ is cyclohexyl.

11. The photochromic compound of claim 1 wherein $R^1$, $R^2$ and $R^3$ are alkyl radicals and all of the $R^4$ and $R^5$ groups are hydrogen.

12. The photochromic compound of claim 11, wherein $R^1$ is methyl or isopropyl and both $R^2$ and $R^3$ are methyl.

* * * * *

UNITED STATES PATENT AND TRADEMARK OFFICE
CERTIFICATE OF CORRECTION

PATENT NO. : 5,233,038
DATED : August 3, 1993
INVENTOR(S) : Robert Guglielmetti et al It is certified that error appears in the above-indentified patent and that said Letters Patent is hereby corrected as shown below:

Claim 1, col. 10, line 12, delete (allkyl), insert --allyl--.

Claim 7, col. 10, line 57, change "R''' " to --$R^{4'''}$--; and line 58, change "R'''' " to --$R^{4''''}$--.

Signed and Sealed this

Eleventh Day of October, 1994

BRUCE LEHMAN

Attest:

Attesting Officer

Commissioner of Patents and Trademarks